United States Patent
Heida et al.

(10) Patent No.: US 11,034,631 B2
(45) Date of Patent: Jun. 15, 2021

(54) METHOD FOR OBTAINING PURE 1,3-BUTADIENE

(71) Applicant: BASF SE, Ludwigshafen am Rhein (DE)

(72) Inventors: Bernd Heida, Ellerstadt (DE); Tobias Keller, Ludwigshafen (DE); Jan-Oliver Weidert, Ludwigshafen (DE)

(73) Assignee: BASF SE, Ludwigshafen am Rhein (DE)

(*) Notice: Subject to any disclaimer, the term of this patent is extended or adjusted under 35 U.S.C. 154(b) by 159 days.

(21) Appl. No.: 16/475,566

(22) PCT Filed: Jan. 24, 2018

(86) PCT No.: PCT/EP2018/051613
§ 371 (c)(1),
(2) Date: Jul. 2, 2019

(87) PCT Pub. No.: WO2018/138100
PCT Pub. Date: Aug. 2, 2018

(65) Prior Publication Data
US 2020/0339490 A1    Oct. 29, 2020

(30) Foreign Application Priority Data
Jan. 25, 2017   (EP) .................................... 17153120

(51) Int. Cl.
*C07C 7/08*    (2006.01)
*B01D 3/14*    (2006.01)
(Continued)

(52) U.S. Cl.
CPC ................ *C07C 7/08* (2013.01); *B01D 3/141* (2013.01); *B01D 3/143* (2013.01); *B01D 3/346* (2013.01);
(Continued)

(58) Field of Classification Search
CPC .. C07C 5/333; C07C 7/05; C07C 5/48; C07C 5/327; B01D 3/40
See application file for complete search history.

(56) References Cited

U.S. PATENT DOCUMENTS

2004/0045804 A1\*  3/2004  Bohner .................... C07C 7/04
                                                         203/1
2004/0065538 A1    4/2004  Bohner et al.
(Continued)

FOREIGN PATENT DOCUMENTS

DE    2 251 051         10/1973
DE    101 05 660 A1     8/2002
(Continued)

OTHER PUBLICATIONS

WO-2013083536-A1_English Translation (Year: 2013).\*
(Continued)

*Primary Examiner* — Youngsul Jeong
(74) *Attorney, Agent, or Firm* — Grüneberg and Myers PLLC

(57) ABSTRACT

Process for isolating pure 1,3-butadiene from a crude $C_4$ fraction by extractive distillation using a selective solvent, wherein (a) the crude $C_4$ fraction is introduced into a predistillation column, a first low boiler fraction comprising $C_3$-hydrocarbons is taken off as overhead stream, a gaseous $C_4$ fraction is taken off as side stream and a first high boiler fraction is taken off as bottom stream, (b) the gaseous $C_4$ fraction is brought into contact with a selective solvent in at least one extraction column, giving an overhead fraction comprising butanes and butenes and a bottom fraction comprising 1,3-butadiene and selective solvent, (c) crude 1,3-butadiene is desorbed from the bottom fraction in at least one stripping column, with a stripped selective solvent being obtained and the stripped selective solvent being recirculated to the extraction column, and (d) at least part of the
(Continued)

crude 1-3-butadiene is fed to a pure distillation column and a second high boiler fraction is separated off and a gaseous purge stream is taken off. Gaseous purge streams from the columns which are necessary in order to keep the concentration of molecular oxygen below a predetermined concentration limit are consolidated with output streams which are in any case provided for discharging other components in the process. The recirculation of the second high boiler fraction to a lower section of the predistillation column creates a further degree of freedom in operation of the pure distillation column.

11 Claims, 1 Drawing Sheet

(51) Int. Cl.
  *B01D 3/34* (2006.01)
  *B01D 11/04* (2006.01)
  *B01D 11/00* (2006.01)

(52) U.S. Cl.
  CPC ...... *B01D 11/0426* (2013.01); *B01D 11/0488* (2013.01); *B01D 11/0492* (2013.01); *B01D 2011/002* (2013.01)

(56) References Cited

U.S. PATENT DOCUMENTS

2008/0228019 A1   9/2008   Heida
2014/0200381 A1*  7/2014   Josch ........................ C07C 7/11
                                                       585/621

FOREIGN PATENT DOCUMENTS

WO   WO 2005/075388 A1   8/2005
WO   WO 2011/110562 A1   9/2011
WO   WO 2013/083536 A1   6/2013
WO   WO-2013083536 A1 * 6/2013 ............. C10G 21/14

OTHER PUBLICATIONS

International Search Report dated Mar. 21, 2018 in PCT/EP2018/051613 filed Jan. 24, 2018.
U.S. Appl. No. 15/741,350, filed Jan. 2, 2018, US2018-0361270, Asprion, Norbert et al.
U.S. Appl. No. 16/349,364, filed May 13, 2019, Parvulescu, Andrei-Nicolae et al.
U.S. Appl. No. 16/318,221, filed Jan. 16, 2019, US2019-0169149, Teles, Joaquim Henrique et al.
U.S. Appl. No. 16/315,345, filed Jan. 4, 2019, Teles, Joaquim Henrique et al.
U.S. Appl. No. 16/315,680, filed Jan. 7, 2019, US2019-0210989, Teles, Joaquim Henrique et al.

* cited by examiner

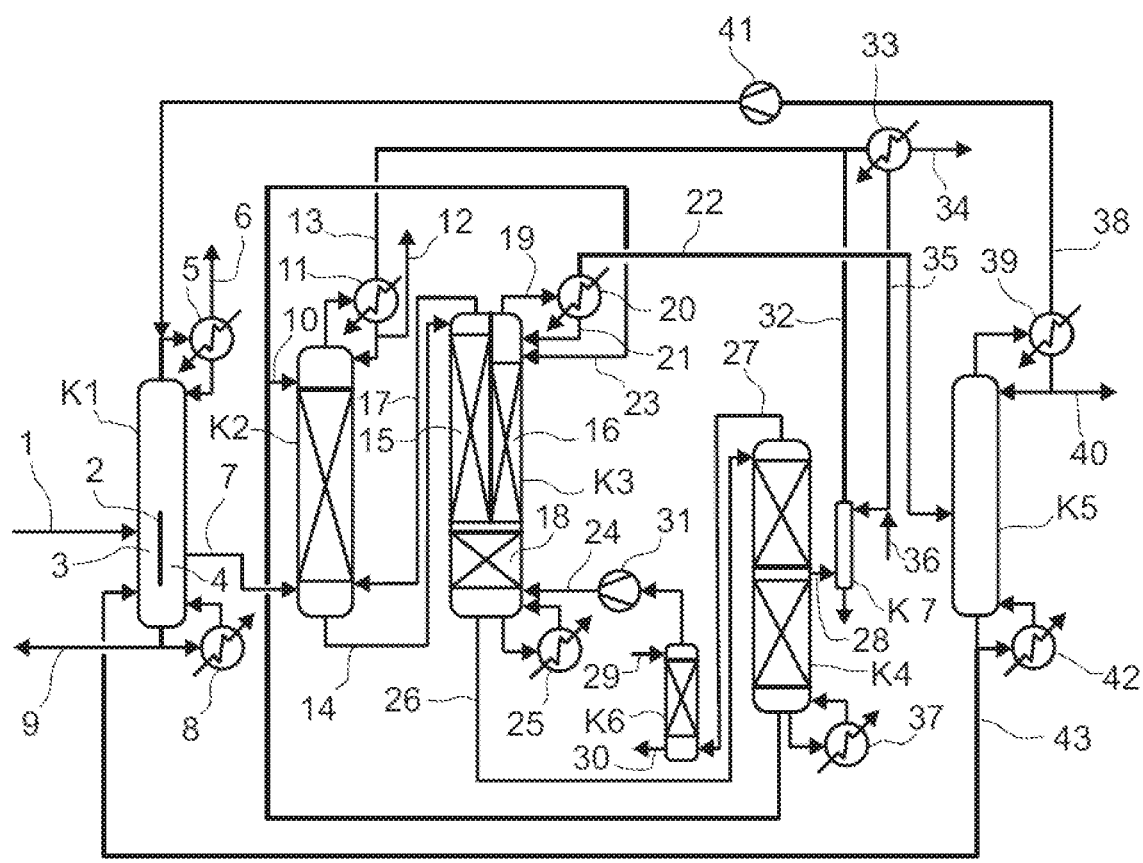

METHOD FOR OBTAINING PURE 1,3-BUTADIENE

The present invention relates to a process for isolating pure 1,3-butadiene from a crude $C_4$ fraction.

1,3-Butadiene is generally obtained industrially from $C_4$ fractions, i.e. mixtures of hydrocarbons in which the $C_4$-hydrocarbons, in particular 1-butene, i-butene and 1,3-butadiene, predominate.

$C_4$ fractions are obtained, for example, in the preparation of ethylene and propylene by thermal cracking, usually in steam crackers, in particular naphtha or gas crackers. Furthermore, 1,3-butadiene-comprising $C_4$ fractions are obtained in the catalytic dehydrogenation of n-butane and/or n-butene. As starting gas mixture for the oxidative dehydrogenation of n-butenes to 1,3-butadiene, it is possible to use any mixture comprising n-butenes. Gas mixtures which comprise n-butenes and are used as starting gas in the oxidative dehydrogenation of n-butenes to 1,3-butadiene can be prepared by nonoxidative dehydrogenation of gas mixtures comprising n-butane. The 1,3-butadiene-comprising $C_4$ fractions will subsequently be referred to as crude $C_4$ fractions. They comprise not only small amounts of $C_3$- and $C_5$-hydrocarbons but generally also acetylene (methylacetylene, ethylacetylene and vinylacetylene).

It is generally known that pure 1,3-butadiene can be isolated from crude $C_4$ fractions by means of a sequence of particular process steps in which a crude 1,3-butadiene is firstly obtained from the crude $C_4$ fraction and the crude 1,3-butadiene is then purified further in order to isolate the pure 1,3-butadiene therefrom. Crude 1,3-butadiene is a mixture comprising from about 90 to 99.5% by weight of 1,3-butadiene, in particular from 98 to 99% by weight of 1,3-butadiene. The required specifications for pure 1,3-butadiene frequently provide for a minimum content of 1,3-butadiene of 99.6% by weight and a maximum permissible content of acetylenes and of 1,2-butadiene of 20 ppm in each case, based on the mass of the pure 1,3-butadiene.

The isolation of 1,3-butadiene from $C_4$ fractions is a complex separation task because of the small differences in the relative volatilities of the components. An extractive distillation, i.e. a distillation with addition of a selective solvent which has a boiling point higher than the mixture to be fractionated and increases the differences in the relative volatilities of the components to be separated, is therefore carried out. The crude 1,3-butadiene obtained in this way is, in order to meet required specifications, purified by distillation to give pure 1,3-butadiene.

For example, according to WO 2011/110562 A1, a crude $C_4$ fraction is selectively hydrogenated, high-boiling constituents are subsequently separated off from the selectively hydrogenated $C_4$ fraction and the remaining $C_4$ fraction is then worked up further by extractive distillation in order to obtain crude 1,3-butadiene. The crude 1,3-butadiene is purified further by pure distillation to give pure 1,3-butadiene.

DE 101 05 660 discloses a process for obtaining crude 1,3-butadiene from a $C_4$ fraction by extractive distillation using a selective solvent. The process is carried out in a dividing wall column (TK) in which a dividing wall (T) is arranged in the longitudinal direction of the column to form a first subregion (A) a second subregion (B) and a lower joint column region (C) and which is preceded by an extractive scrubbing column (K).

According to WO 2013/083536, a gaseous purified crude $C_4$ fraction is provided as feed stream for an extractive distillation in which the liquid crude $C_4$ fraction is introduced in the upper third of a distillation column to form an enrichment section and a stripping section and an overhead stream comprising $C_3$-hydrocarbons, a bottom stream comprising $C_4$-oligomers and -polymers and the $C_{5+}$-hydrocarbons are taken off from the distillation column and the gaseous purified crude $C_4$ fraction is taken off as side stream from the stripping section.

It is common to all the processes for extractive distillation of C4 fractions using selective solvents that the selective solvent becomes loaded with the components of the $C_4$ fraction to which it has a greater affinity by countercurrent conducting of the $C_4$ fraction to be fractionated in vapor form with the liquid selective solvent under suitable thermodynamic conditions, generally at low temperatures, usually in the range from 20 to 80° C., and at moderate pressures, frequently from about 3 to about 6 bar, while the components with which the selective solvent has a lower affinity remain in the vapor phase and are taken off as overhead stream. The components are subsequently fractionally liberated from the selective solvent in the loaded solvent stream under suitable thermodynamic conditions, i.e. at higher temperature and/or lower pressure.

1,3-Butadiene is a polymerizable compound and can form undesirable polymeric deposits in various regions of the plant; these deposits can, depending on molecular weight and degree of crosslinking, be rubber-like or brittle (known as popcorn polymers). The rubber-like deposits hinder heat transfer and lead to a reduction in cross sections of conduits. The formation of popcorn polymers can cause severe damage in the interior of the plant and lead to bursting of condensers and conduits. The deposits have to be removed regularly from columns and pipes with great effort and downtimes which result in losses.

The presence of small amounts of molecular oxygen in the lower ppm range or below has been recognized as a main cause of the formation of the polymers. Molecular oxygen can, e.g. via butadiene peroxide or hematite as free-radical initiator, trigger the free-radical polymerization of 1,3-butadiene. Molecular oxygen gets into the plant through the smallest leaks in the plant parts and via the streams introduced into the process.

In order to keep the oxygen content below a predetermined concentration limit, part of the gas phase can be discharged as purge stream (vent) from the process periodically or continuously from the various condensers where oxygen, nitrogen and other inert gases concentrate. A considerable amount of product of value is lost from the process with the purge stream in addition to molecular oxygen and inert gases which are comprised therein only in a very low concentration. It is therefore essential to monitor the oxygen content by means of oxygen detectors in the relevant plant parts and limit the purge streams to the volume necessary to keep the oxygen content below the concentration limit and at the same time keep the $C_4$ loss to a minimum. It is thus possible to empirically determine a gas volume which is allowed to be deliberated vented from the plant. In the case of controlled discharge of purge streams on the basis of the oxygen measurement, residual oxygen contents of 3-10 ppm in the purge stream are usually prescribed. A disadvantage is that the oxygen detectors are susceptible to malfunctions and require a high degree of maintenance.

In most cases, a gas comprising $C_4$-acetylenes is also desorbed separately from the crude 1-3-butadiene in the extractive distillation processes. Since $C_4$-acetylenes are chemically unstable and explosive, it is normal practice, for safety reasons, to dilute the gas comprising $C_4$-acetylenes with another internal process stream so that the concentration of $C_4$-acetylenes remains reliably below the decomposition hazard concentration, e.g. at 30-40% by volume at 1.7 bar absolute. For example, a vapor stream comprising essentially raffinate 1 from the extraction column is used as diluent gas. The diluted gas comprising $C_4$-acetylenes is usually mixed into the cracker feedstock, sometimes utilized thermally or sent to a flare.

It is an object of the present invention to provide an efficient process for isolating pure 1,3-butadiene from a crude $C_4$ fraction, in particular a process in which production operation can be maintained for a long time and a high yield of pure 1,3-butadiene is nevertheless achieved.

The object is achieved by a process for isolating pure 1,3-butadiene from a crude $C_4$ fraction by extractive distillation using a selective solvent, wherein a) the crude $C_4$ fraction is introduced into a predistillation column, a low boiler fraction comprising $C_3$-hydrocarbons is taken off as overhead stream, a gaseous $C_4$ fraction is taken off as side stream and a first high boiler fraction is taken off as bottom stream, b) the gaseous $C_4$ fraction is brought into contact with a selective solvent in at least one extraction column, giving an overhead fraction comprising butanes and butenes and a bottom fraction comprising 1,3-butadiene and selective solvent, c) crude 1,3-butadiene is desorbed from the bottom fraction in at least one stripping column, with a stripped selective solvent being obtained and the stripped selective solvent being recirculated to the extraction column, and d) at least part of the crude 1-3-butadiene is fed to a pure distillation column and a second high boiler fraction is separated off and a gaseous purge stream is taken off.

For reasons of capital costs, it can be advantageous not to use one extraction column but instead to couple two columns in such a way that they correspond thermodynamically to a column having twice the number of theoretical plates. The extraction column and the stripping column can also each be integrated entirely or partly into an integrated extraction and stripping column. The extraction column and stripping column can be preceded by (a) further extraction column(s) and/or be followed by (a) further stripping column(s). If a further stripping column is installed downstream of the integrated extraction and stripping column, reference will be made to an extraction and prestripping column in the case of the integrated column in the present document.

In the preferred embodiments of the process of the invention, gaseous purge streams from the columns, which are necessary to keep the concentration of molecular oxygen below a predetermined concentration limit, are consolidated to outlets which are in any case provided for discharge of other components in the process. Since the streams concerned are large streams in terms of volume compared to conventional purge streams, it is possible to keep the oxygen content reliably below the detection limit of oxygen detectors customary in industry instead of the customary, monitored 3-10 ppm.

The purge stream from the pure distillation column is preferably conveyed together with the vapor from the predistillation column through the overhead condenser of the predistillation column. This allows the volume flow of the purge stream from the pure distillation column to be run up in order to serve as outlet for traces of oxygen in the pure distillation column and push the oxygen content in the pure distillation column to below the detection limit of conventional oxygen detectors. 1,3-Butadiene comprised in the purge stream from the pure distillation column condenses in the overhead condenser of the predistillation column and is kept in the process.

A dedicated purge stream from the stripping column in which crude 1,3-butadiene is desorbed becomes dispensable when the crude 1,3-butadiene is taken off in gaseous form from the stripping column and is fed in gaseous form into the pure distillation column. Here, the desorbed crude 1,3-butadiene is partly condensed, the condensed part of the crude 1,3-butadiene is conveyed as runback into the stripping column and/or into an after-scrubbing zone described below and the other part of the crude 1,3-butadiene is fed in gaseous form into the pure distillation column. The volume flow of the crude 1,3-butadiene taken off in gaseous form is many times the volume flow of a conventional purge stream for oxygen; in this way, the oxygen content in the stripping column can be pushed to below the detection limit of conventional oxygen detectors.

Furthermore, it is proposed that a stream which simultaneously serves as purge stream for oxygen and inert gases from the extraction column be used as diluent gas for $C_4$-acetylenes. The gas comprising $C_4$-acetylenes is preferably diluted with uncondensed constituents of the vapor from the extraction zone, i.e. the outlet is arranged not in the vapor space of the extraction column but at or downstream of the condenser of the extraction column, so that this simultaneously serves as oversized purge stream. C4 losses via the purge stream thus no longer occur.

The crude $C_4$ fraction is generally introduced in liquid form into the predistillation column. A low boiler fraction comprising $C_3$-hydrocarbons is taken off as overhead stream. A gaseous $C_4$ fraction is taken off as side stream from the predistillation column. A first high boiler fraction is taken off as bottom stream from the predistillation column. The predistillation column simultaneously effects prepurification and vaporization of the crude $C_4$ fraction. A separate vaporizer for the purified crude $C_4$ fraction is no longer necessary. The predistillation column can, for example, be operated at a temperature at the bottom of from 50 to 80° C. and at a pressure of from 4 to 8 bar. All the pressures indicated in the present document are absolute pressures.

The main proportion of the $C_{5+}$-hydrocarbons comprised in the crude $C_4$ fraction and the $C_4$-oligomers and -polymers comprised in the crude $C_4$ fraction can be discharged via the first high boiler fraction. Since a smaller amount of $C_{5+}$ components, in particular polymerizable $C_5$-dienes such as isoprene or cis-2-pentadiene, is conveyed from the predistillation to the extractive distillation, these accumulate to a lesser extent in the selective solvent. Carbonyls such as formaldehyde, acetaldehyde, propionaldehyde, n-butyraldehyde, crotonaldehyde, acetone, methyl ethyl ketone or acrolein are also discharged via the first high boiler fraction.

The liquid crude $C_4$ fraction is advantageously fed to the predistillation column at the side to form an enrichment section located above the inlet and a stripping section located below the inlet. The predistillation column is preferably a tray column. The tray column has, in particular, from 30 to 100 practical trays or particularly preferably from 50 to 70 practical trays. The side inlet preferably divides the number of trays located higher up and the number of trays located lower down in a ratio of from 20:80 to 80:20.

In a preferred embodiment, the predistillation column is divided in a middle section by a dividing wall aligned essentially in the longitudinal direction of the predistillation column into an inflow region and a side offtake region. The liquid crude $C_4$ fraction is introduced into the inflow region and the gaseous $C_4$ fraction is taken off from the side offtake region. The components of the crude $C_4$ fraction cannot get directly to the side offtake and into the side stream since they are separated from down-flowing condensate and ascending vapor on flowing over the lower or upper edge of the dividing wall. The dividing wall generally extends over from 4 to 40 trays, preferably over from 6 to 30 trays.

In an alternative embodiment, the predistillation column can also be configured as a distillation column without dividing wall. The gaseous $C_4$ fraction is then taken off below the inlet for the crude $C_4$ fraction. This ensures that the components of the crude $C_4$ fraction do not get directly to the side offtake and into the side stream.

The gaseous purified $C_4$ fraction thus obtained is brought into contact with a selective solvent in at least one extraction column, giving an overhead fraction comprising butanes and butenes and a bottom fraction comprising 1,3-butadiene, $C_4$-acetylenes and selective solvent. The gaseous $C_4$ fraction is normally brought into contact with the selective solvent by conveying the gaseous $C_4$ fraction in countercurrent to the selective solvent in at least one section of the extraction column(s).

Pressure and temperature are set in the extraction column in such a way that those components of the $C_4$ fraction for which the selective solvent has a lower affinity than for 1,3-butadiene, in particular the butanes and the butenes, remain mostly in the gas phase while 1,3-butadiene and acetylenes and further hydrocarbons for which the selective solvent has a greater affinity than for 1,3-butadiene are essentially completely absorbed by the selective solvent. The extraction column can, for example, be operated at a temperature of from 20 to 80° C. and at a pressure of from 3 to 6 bar. In this way, the overhead fraction comprising butanes and butenes and the bottom fraction comprising 1,3-butadiene, $C_4$-acetylenes and selective solvent are obtained. Butanes and butenes are taken off at the top. The overhead fraction is usually referred as raffinate 1.

The bottom fraction comprises not only the solvent and 1,3-butadiene but generally also further hydrocarbons for which the selective solvent has a greater affinity than for 1,3-butadiene, e.g. $C_4$-acetylenes. For this reason, a fractional desorption in which the hydrocarbons absorbed in the selective solvent are desorbed in the reverse order of their affinity for the selective solvent is normally carried out. Accordingly, not only crude 1,3-butadiene but preferably also a gas comprising $C_4$-acetylenes, in particular vinylacetylene, as separate fraction are desorbed from the bottom fraction.

In one embodiment, the bottom fraction is introduced into an extraction and prestripping column. The upper part of the extraction and prestripping column acts as stripping section in which the butanes and butenes still dissolved in the solvent and also other low boilers can be driven off and taken off at the top. The overhead product from the extraction and prestripping column can be fed back into the extraction column. Crude 1,3-butadiene, which comprises 1,3-butadiene together with small amounts of methylacetylene, 1,2-butadiene and $C_{5+}$-hydrocarbons, can be taken off as side offtake stream from the extraction and prestripping column. Prestripped solvent, which still comprises various $C_4$ components such as vinylacetylene, is obtained at the bottom of the extraction and prestripping column. The extraction and prestripping column can, for example, be operated at a temperature at the bottom of from 20 to 80° C. and at a pressure of from 3 to 6 bar.

The prestripped solvent obtained in the bottoms from the extraction and prestripping column is preferably conveyed into a stripping column in which further hydrocarbons for which the selective solvent has a greater affinity than for 1,3-butadiene, e.g. $C_4$-acetylenes, are desorbed. The stripping column can, for example, be operated at a temperature of from 120 to 200° C. and at a pressure of from 1.2 to 6 bar.

The gas comprising $C_4$-acetylenes is preferably taken off as side offtake stream from the stripping column. For example, the gas comprising $C_4$-acetylenes which is taken off as side offtake stream from the stripping column can be scrubbed with water in an acetylene scrubber in order to recover selective solvent. The acetylene scrubber can be configured as side column of the stripping column. The scrubbing water can be recycled to the solvent circuit, e.g. into the stripping column and/or the extraction and prestripping column. Water vapor which is entrained by the scrubbed gas comprising $C_4$-acetylenes can be condensed out and recirculated in its entirety or partly to the acetylene scrubber.

To recover that part of the 1,3-butadiene which is desorbed only in the stripping column, the overhead product from the stripping column can be compressed and recirculated to the extraction and prestripping column. The overhead product from the stripping column is suitably cooled before compression, e.g. by means of a direct cooler.

A stripped selective solvent is obtained at the bottom of the stripping column, and this can be used firstly for heat recovery and, after final cooling, be recirculated to the extraction column and optionally to an after-scrubbing zone as described below.

In general, the crude 1,3-butadiene is treated with stripped selective solvent in an after-scrubbing zone. This has the advantage that the $C_4$-acetylenes still comprised in the crude 1,3-butadiene are scrubbed out before the crude 1,3-butadiene goes into the pure distillation column. The solvent running down from the after-scrubbing zone can be introduced into the extraction and prestripping column.

The after-scrubbing zone can be formed by a separate column, e.g. a side column assigned to the extraction and prestripping column. In an appropriate embodiment, the after-scrubbing zone is formed by an upper section of the extraction and prestripping column separated off by a dividing wall which runs essentially in the longitudinal direction of the column. In an upper region of the extraction and prestripping column, a dividing wall is then arranged in the longitudinal direction of the column to form a first upper section serving for extraction, a second upper section forming the after-scrubbing zone and a third section which adjoins the dividing wall at the bottom and serves for desorption. The dividing wall is preferably arranged non-centrally in such a way that the cross-sectional area of the after-scrubbing zone is smaller than the cross-sectional area of the extraction zone.

At least part of the crude 1,3-butadiene is fed to a pure distillation column. In the pure distillation column, pure 1,3-butadiene is isolated with a second high boiler fraction being separated off. The second high boiler fraction is taken off from the bottom of the pure distillation column. In addition, a purge stream is taken off from the pure distillation column. The purge stream from the pure distillation column consists essentially of 1,3-butadiene with traces of water vapor, oxygen and inert gases. The purge stream from the pure distillation column serves to discharge oxygen and inert gases.

The pure distillation column can, for example, be operated at a temperature at the bottom of from 40 to 80° C. and at a pressure from 2 to 8 bar.

The purge stream from the pure distillation column can be taken off at the top of the pure distillation column and the pure 1,3-butadiene can be taken off as side stream from the pure distillation column. In this way, pure 1,3-butadiene having a water content which is lower than the physical solubility of water in 1,3-butadiene can be obtained.

In an advantageous embodiment, the purge stream and pure 1,3-butadiene are taken off together as overhead vapor from the pure distillation column and pure 1,3-butadiene and water are condensed out from the overhead vapor. The uncondensed constituents are discharged as purge stream from the pure distillation column or recirculated as described below. A substream of the condensed pure 1,3-butadiene is, after phase separation, introduced as runback into the pure distillation column, and the other part is taken off as pure 1,3-butadiene. The water content of the pure 1,3-butadiene obtained in this way corresponds to the physical solubility of water in 1,3-butadiene.

In a preferred embodiment of the process of the invention, the purge stream from the pure distillation column is conveyed together with the vapor from the predistillation column through the overhead condenser of the predistillation column. In general, the pure distillation column is operated at a somewhat lower pressure than the predistillation column. The purge stream is then actively conveyed, e.g. by means of a blower or a compressor, from the pure distillation column in order to convey it against the pressure gradient. The purge stream from the pure distillation column can, for example, be introduced into the predistillation column at the top or into the feed conduit to the condenser. This embodiment allows the volume flow of the purge stream from the pure distillation column to be increased within wide limits in order to serve as purge stream for traces of oxygen in the pure distillation column and to push the oxygen content in the pure distillation column to below the detection limit of conventional oxygen detectors. Finally, the purge stream also serves as outlet for oxygen. This reduces the polymerization tendency of the 1,3-butadiene present in the pure distillation column, as a result of which production operation can in turn be maintained for longer. 1,3-Butadiene comprised in the purge stream from the pure distillation column is not lost in this mode of operation. The overhead condenser of the predistillation column is operated so that $C_3$-hydrocarbons are separated off as overhead stream, while higher hydrocarbons are condensed and introduced as runback into the predistillation column. The 1,3-butadiene therefore condenses completely per mass balance in the overhead condenser of the predistillation column, flows into the predistillation column and forms part of the gaseous $C_4$ fraction taken off therefrom as side stream.

In a preferred embodiment of the process of the invention, the second high boiler fraction is recirculated into a lower section of the predistillation column. 1,3-Butadiene optionally comprised in the second high boiler fraction is not lost in this mode of operation. This creates a further degree of freedom in operation of the pure distillation column, e.g. the opportunity of reacting flexibly to a change in composition of the crude $C_4$ fraction and minimizing the energy consumption of the plant. It is possible to heat the bottom of the pure distillation column more flexibly. If it is found, for example, that the content of high-boiling impurities in the pure 1,3-butadiene obtained increases, the heat supply to the bottom of the pure distillation column can be reduced. This results in the high boilers being driven off less strongly in the pure distillation column. However, 1,3-butadiene is then driven off more strongly. As a result, the content of pure 1,3-butadiene increases in the bottoms from the pure distillation column. However, this not lost since the second high boiler fraction collecting at the bottom of the column is not discarded but is instead, in this preferred embodiment, recirculated to the lower section of the predistillation column. Losses of pure 1,3-butadiene which otherwise typically occur when the heat supply to the bottom of the pure distillation column is reduced are thus avoided thereby. Under realistic operating conditions, which occasionally make adjustment of bottom heating necessary, this offers the additional advantage of a further increase in the yield of pure 1,3-butadiene, based on the 1,3-butadiene comprised in the crude $C_4$ fraction, without the purity of the pure 1,3-butadiene being impaired. This makes the process more efficient and enables it to be operated more simply and more flexibly because of the additional degree of freedom.

In a further preferred embodiment, the crude 1,3-butadiene which is fed to the pure distillation column is taken off in gaseous form from the extraction and prestripping column and introduced in gaseous form into the pure distillation column. If an after-scrubbing zone is provided, there is a continuous gas path from the extraction and prestripping column through the after-scrubbing zone to the pure distillation column. The crude 1,3-butadiene is partially condensed in a partial condenser and the condensed part of the crude 1,3-butadiene is fed as runback into the column or into the after-scrubbing zone. The uncondensed part of the crude 1,3-butadiene is fed in gaseous form to the pure distillation column. A gaseous purge stream from the extraction and prestripping column is then no longer necessary since molecular oxygen and inert gases are taken off with the gaseous crude 1,3-butadiene. The volume flow of the crude 1,3-butadiene taken off in gaseous form is many times the volume flow of a conventional purge stream for oxygen and inert gases; the oxygen content in the extraction and prestripping column can thus be pushed to below the detection limit of conventional oxygen detectors. The purge stream from the pure distillation column serves as output for the molecular oxygen introduced via the gaseous crude 1,3-butadiene into the pure distillation column. This embodiment is thus particularly preferred when the purge stream from the pure distillation column is conveyed together with the vapor from the predistillation column through the overhead condenser of the predistillation column. An additional introduction of molecular oxygen into the pure distillation column can then be compensated for particularly economically by increasing the amount of the purge stream taken off at the top of the pure distillation column and thus taking off more molecular oxygen via this.

In a further preferred embodiment, a gaseous purge stream from the extraction column is provided. The outlet is preferably arranged at or downstream of the condenser, e.g. at the distillate collector, i.e. the remaining gas constituents which are not condensed in the overhead condenser of the extraction column are discharged. These uncondensed constituents consist essentially of butanes, butenes, inert gas such as nitrogen and minor amounts of molecular oxygen. The purge stream from the extraction column can advantageously be used for diluting the gas which is desorbed in the stripping column and comprises $C_4$-acetylenes.

The crude $C_4$ fraction comprises at least 1,3-butadiene, butanes, butenes and $C_4$-acetylenes. In many cases, the crude $C_4$ fraction comprises 1,3-butadiene, butanes, butenes and $C_4$-acetylenes, $C_3$-hydrocarbons and $C_{5+}$-hydrocarbons.

The crude $C_4$ fraction is, for example, a crude $C_4$ fraction from a naphtha cracker.

A typical crude $C_4$ fraction from a naphtha cracker has the following composition in percent by weight:

| | |
|---|---|
| propane | 0-0.5 |
| propene | 0-0.5 |
| propadiene | 0-0.5 |
| propyne | 0-0.5 |
| n-butane | 3-10 |
| i-butane | 1-3 |
| 1-butene | 10-20 |
| i-butene | 10-30 |
| trans-2-butene | 2-8 |
| cis-2-butene | 2-6 |
| 1,3-butadiene | 15-85 |
| 1,2-butadiene | 0.1-1 |
| ethylacetylene | 0.1-2 |
| vinylacetylene | 0.1-3 |
| $C_5$-hydrocarbons | 0-0.5 |

Crude $C_4$ fractions from naphtha crackers thus comprise predominantly butanes, butenes and 1,3-butadiene. In addition, small amounts of other hydrocarbons are comprised. $C_4$-acetylenes are frequently comprised in a proportion of up to 5% by weight of even up to 2% by weight.

Possible selective solvents are substances or mixtures in general which have a boiling point higher than that of the mixture to be fractionated and also a greater affinity for conjugated double bonds and triple bonds than for single double bonds and single bonds, preferably dipolar solvents, particularly preferably dipolar aprotic solvents. For engineering reasons, preference is given to substances which are not corrosive or have little corrosivity. Suitable selective solvents for the process of the invention are, for example, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, in particular N-methylpyrrolidone (NMP). In general, N-alkyl-substituted lower aliphatic acid amides or N-alkyl-substituted cyclic acid amides are used. Dimethylformamide, acetonitrile, furfural and in particular N-methylpyrrolidone are particularly advantageous.

However, it is also possible to use mixtures of these solvents with one another, for example of N-methylpyrrolidone with acetonitrile, mixtures of these solvents with cosolvents such as water, alcohols, in particular those having 5 or fewer carbon atoms, e.g. methyl alcohol, ethyl alcohol, n-propyl alcohol, isopropyl alcohol, n-butyl alcohol, isobutyl alcohol, sec-butyl alcohol, tert-butyl alcohol, n-pentyl alcohol, or alicyclic alcohols such as cyclopentanol, diols, such as ethylene glycol and/or tert-butyl ethers, for example methyl tert-butyl ether, ethyl tert-butyl ether, propyl tert-butyl ether, n-butyl or isobutyl tert-butyl ether.

In a preferred embodiment of the process of the invention, the selective solvent comprises at least 80% by weight of N-methylpyrrolidone. The selective solvent preferably comprises from 85 to 95% by weight of NMP and from 5 to 15% by weight of water. N-methylpyrrolidone, preferably in aqueous solution, in particular with from 7 to 9% by weight of water, particularly preferably with 8.3% by weight of water, is particularly suitable.

In addition, the selective solvent can further comprise, in particular, auxiliaries, inhibitors, antifoams, organic secondary components as impurity.

The invention will be illustrated in detail by the accompanying drawing and the following examples.

The FIGURE schematically shows a preferred plant for carrying out the process of the invention.

A liquid crude $C_4$ fraction, stream 1, is introduced into the predistillation column K1. The predistillation column K1 is divided, in a middle section, by a dividing wall 2 aligned essentially in the longitudinal direction of the predistillation column K1 into an inflow region 3 and a side offtake region 4. The inflow region 3 and the side offtake region 4 each extend in the vertical direction from the upper to the lower end of the dividing wall 2. A gaseous $C_4$ fraction 7 is taken off from the side offtake region 4. The vapor from the predistillation column K1 is passed through the overhead condenser 5. The condensate formed therein is fed back into the predistillation column K1. The uncondensed part of the vapor forms the overhead stream 6 which is taken off as a low boiler fraction from the predistillation column K1. In addition, a first high boiler fraction is taken off as bottom stream 9 from the predistillation column K1. The bottom of the predistillation column K1 is heated by means of the vaporizer 8.

The gaseous $C_4$ fraction 7 is introduced into a lower section of an extraction column K2 and is brought into contact therein with a stripped selective solvent 10 which is fed into an upper section of the extraction column K2. Condensation of the vapor from the extraction column K2 in the condenser 11 gives an overhead fraction 12 (known as raffinate I) comprising butanes and butenes and also an uncondensed part 13 of the vapor. The stream 13 serves as the diluent gas necessary for safety reasons for the acetylenes 32. At the same time, the stream 13 is the purge stream for the extraction column K2 in order to control the content of molecular oxygen in the gas space of the extraction column K2 and keep it below the detection limit. In addition, a bottom fraction 14 which consists essentially of selective solvent in which 1,3-butadiene and also methylacetylene, vinylacetylene, ethylacetylene and $C_{5+}$-hydrocarbons are dissolved is obtained.

The bottom fraction 14 is fed into an upper section 15 of an extraction and prestripping column K3. A substantial part of the crude 1,3-butadiene is desorbed in the lower section 18 of the extraction and prestripping column K3. The crude 1,3-butadiene is brought into contact with stripped selective solvent 23 in an after-scrubbing zone in order to separate off $C_4$-acetylenes. The after-scrubbing zone is an upper section 16 of the extraction and prestripping column K3 which is separated off by a dividing wall running essentially in the longitudinal direction of the column. The crude 1,3-butadiene 19 discharged at the top of the extraction and prestripping column K3 from the scrubbing section located immediately above the after-scrubbing zone is partially condensed in the condenser 20. The condensed part 21 of the crude 1,3-butadiene is conveyed as runback into the scrubbing section via which the runback flows into the after-scrubbing zone. The other part 22 of the crude 1,3-butadiene is fed in gaseous form to the pure distillation column K5. The bottom of the extraction and prestripping column K3 is heated by means of the vaporizer 25.

A gas 17 comprising butanes and butenes which is discharged from section 15 at the top of the extraction and prestripping column K3 is conveyed back into a lower section of the extraction column K2. Thermodynamically, the section 15 of the extraction and prestripping column K3 and the extraction column K2 together correspond to a single extraction column, which for reasons of the column height has been divided in two vertically.

Predegassed solvent from the bottom of the extraction and prestripping column K3 is conveyed further as stream 26 into a stripping column K4. In the stripping column K4, further crude 1,3-butadiene is desorbed and this is conveyed via conduit 27, the direct cooler K6, the compression 31 and conduit 24 into the lower section of the extraction and prestripping column K3. Cooling medium is introduced and discharged via the conduits 29 and 30. Intrinsic condensate, which consists essentially of components of the selective solvent, e.g. water and NMP, serves as cooling medium. The bottom of the stripping column K4 is heated by means of the vaporizer 37.

A gas 28 comprising $C_4$-acetylenes is taken off as side offtake stream from the stripping column K4. In the acetylene scrubber K7, the gas 28 comprising $C_4$-acetylenes is scrubbed with water introduced via conduit 36. The stream 32 obtained at the top of the acetylene scrubber K7 is diluted with the purge stream 13 from the extraction column K2. Condensed constituents are condensed in the condenser 33 and can partly be introduced as runback 35 into the acetylene scrubber K7; the remainder is essentially process wastewater. Uncondensed constituents are discharged as stream 34 (diluted acetylene stream).

In the pure distillation column K5, a second high boiler fraction 43 is separated off from the crude 1,3-butadiene 22. The vapor is introduced into the condenser 39. The uncondensed part of the vapor forms the purge stream 38. The pure 1,3-butadiene is obtained as condensate in the condenser 39 and is taken off as stream 40; a substream is introduced as runback into the pure distillation column K5. The bottom of the pure distillation column K5 is heated by means of the vaporizer 42.

The second high boiler fraction 43 is recirculated into a lower section of the predistillation column K1. The deaeration stream 38 is conveyed via the blower 41 to the vapor of the predistillation column K1.

EXAMPLE 1

The process of the invention was simulated on the basis of a plant as shown in the FIGURE. The BASF in-house software Chemasim was used for the simulation calculation; comparable results would be obtained using commercially available software such as Aspen Plus (manufacturer: AspenTech, Burlington/Mass., USA) or PRO II (Fullerton, USA). The set of parameters was based on comprehensive equilibrium measurements, studies on laboratory columns and operating data from various plants. The target specification for the pure 1,3-butadiene was: at least 99.5% of 1,3-butadiene, not more than 20 ppm of 1,2-butadiene, not more than 20 ppm of acetylenes.

A crude $C_4$ fraction comprising 1300 ppm of $C_3$-hydrocarbons, 2.0% of n-butane, 0.6% of isobutane, 19.0% of n-butene, 28.3% of isobutene, 5.5% of trans-2-butene, 4.4% of cis-2-butene, 39.0% of 1,3-butadiene, 0.2% of 1,2-butadiene, 1200 ppm of 1-butyne, 4500 ppm of vinylacetylene and 3000 ppm in each case of $C_5$-hydrocarbons was taken as starting point.

Table 1 summarizes the mass flows and compositions of relative streams. The designations of these streams in the table relate to the designations in FIG. 1.

TABLE 1

| Example 1 | Stream | | | |
|---|---|---|---|---|
| | 1 | 7 | 9 | 43 |
| Mass flow [kg/h] | 32 000 | 31 935 | 200 | 37 |
| 1,2-Butadiene [% by weight] | 0.15 | 0.07 | 12.13 | 40.00 |
| Acetylenes [% by weight] | 0.57 | 0.57 | 0.38 | 0.20 |
| $C_{5+}$ components [% by weight] | 0.30 | 0.02 | 45.00 | 8.97 |
| 1,3-Butadiene [% by weight] | | | 3.63 | 35.94 |

A loss of 1,3-butadiene of about 7 kg/h results from the single high boiler purge stream 9. The content of $C_5$ components as the high boilers which are most difficult to separate off is reduced by about 94% in the predistillation column.

COMPARATIVE EXAMPLE 2

A process according to the prior art was simulated. The composition of the crude $C_4$ fraction and the target specification for the pure 1,3-butadiene were the same as in example 1. The plant used as a basis had a preceding distillation column as per WO 2013/083536 A1 to which the liquid crude $C_4$ fraction was fed instead of the predistillation column K1 provided with the dividing wall 2. Recirculation of the high boiler fraction from the pure distillation column into the predistillation column is not provided.

Table 2 summarizes the mass flows and compositions of relevant streams.

TABLE 2

| Comparative example 2 | Stream | | | |
|---|---|---|---|---|
| | Crude $C_4$ liq.[1] | Crude $C_4$ purif.[2] | Bottoms dist..[3] | Bottoms pure[4] |
| Mass flow [kg/h] | 32 000 | 31 743 | 110 | 69 |
| 1,2-Butadiene [% by weight] | 0.15 | 0.14 | 40.00 | 40.00 |
| Acetylenes [% by weight] | 0.57 | 0.57 | 0.21 | 0.18 |
| $C_{5+}$ components [% by weight] | 0.30 | 0.13 | 8.38 | 30.18 |
| 1,3-Butadiene [% by weight] | | | 29.88 | 14.88 |

[1] liquid crude $C_4$ fraction (reference symbol 1 in FIG. 1 of WO 2013/083536 A1)
[2] vaporous purified crude $C_4$ fraction (reference symbol 4 in FIG. 1 of WO 2013/083536 A1)
[3] bottom stream obtained from the upstream distillation column (reference symbol 3 in FIG. 1 of WO 2013/083536 A1)
[4] bottom stream obtained in the pure distillation In this process, two $C_{5+}$-comprising high boiler streams which are discarded are obtained: the bottom stream from the upstream distillation column and the bottom stream obtained in the pure distillation. There is a loss of 1,3-butadiene of about 43 kg/h. In the upstream distillation column of comparative example 2, only a small proportion of the components was separated off (55%). A far higher proportion of the $C_{5+}$ components was carried via the gaseous purified crude $C_4$ fraction into the extraction column.

EXAMPLE 3

Comparison of the Purge Streams for Removal of Oxygen

Table 3 compares the mass flows of the conventional purge streams for removal of oxygen with the internal streams proposed according to the invention for the removal of oxygen. The table illustrates that replacement of purge streams by internal streams enables the mass flow thereof to be multiplied without loss of product of value. Total gases comprising from about 30 to 60 kg of 1,3-butadiene are typically discharged per hour via the purge streams customary according to the prior art. The streams 13, 22 and 38 each replace one purge stream in the plant of the FIGURE. Nevertheless, the loss of product of value occurring via these streams is lower since the streams are recirculated into the process. Increasing the mass flows from 10-20 kg/h to 360 kg/h, 18 376 kg/h and 360 kg/h, respectively, results in more oxygen being discharged from the columns. As a result, the oxygen content can be pushed to below the detection limit of conventional detectors and the undesirable polymerization tendency of 1,3-butadiene can consequently also be reduced.

TABLE 3

|  | Prior art Purge stream at | Process according to the invention (The FIGURE) Stream | |
|---|---|---|---|
| Top of the extraction column | 10-20 kg/h | 13 | 360 kg/h |
| Top of the extraction and prestripping column | 10-20 kg/h | 22 | 18 376 kg/h |
| Top of the pure distillation column | 10-20 kg/h | 38 | 200 kg/h |
| Total Loss | 30-60 kg/h 30-60 kg/h | Total Loss | 18 936 kg/h 0 |

The invention claimed is:

1. A process for isolating pure 1,3-butadiene from a crude $C_4$ fraction by extractive distillation using a selective solvent, the process comprising:
   a) introducing a liquid crude $C_4$ fraction into an inflow region of a predistillation column, which is divided in a middle section by a dividing wall aligned essentially in a longitudinal direction of the predistillation column into the inflow region and a side offtake region, taking off a first low boiler fraction comprising $C_3$-hydrocarbons as an overhead stream, taking off a gaseous $C_4$ fraction as a side stream from the side offtake region and taking off a first high boiler fraction as a bottom stream,
   b) bringing the gaseous $C_4$ fraction into contact with a selective solvent in at least one extraction column, to obtain an overhead fraction comprising butanes and butenes and a bottom fraction comprising 1,3-butadiene and the selective solvent,
   c) desorbing crude 1,3-butadiene from the bottom fraction in at least one stripping column, thereby obtaining selective solvent from the bottom fraction and recirculating the selective solvent which was obtained from the bottom fraction in the at least one stripping column to the at least one extraction column, and
   d) feeding at least part of the crude 1-3-butadiene to a pure distillation column, separating off a second high boiler fraction, taking off a gaseous purge stream, obtaining the pure 1,3-butadiene from a vapor fraction from the pure distillation column, and recirculating the second high boiler fraction to a lower section of the predistillation column below the inflow region for the liquid crude $C_4$ fraction.

2. The process of claim 1, wherein the gaseous purge stream from the pure distillation column is conveyed together with a vapor from the predistillation column through an overhead condenser of the predistillation column.

3. The process of claim 1, wherein the crude 1,3-butadiene is brought into contact with the selective solvent in an after-scrubbing zone.

4. The process of claim 2, wherein the desorbed crude 1,3-butadiene is partially condensed, a condensed part of the crude 1,3-butadiene is conveyed as runback into the at least one stripping column and/or into an after-scrubbing zone and the remaining part of the crude 1,3-butadiene after condensation is fed in gaseous form to the pure distillation column.

5. The process of claim 1,
   wherein the gaseous $C_4$ fraction is brought into contact with the selective solvent in an extraction column and in an upper section of an extraction and prestripping column on a first side of a dividing wall running essentially in a longitudinal direction of the extraction and prestripping column, and
   the crude 1,3-butadiene is desorbed from the bottom fraction in a lower section below the dividing wall of the extraction and prestripping column and from a stripping column.

6. The process of claim 5, wherein an after-scrubbing zone is an upper section of the extraction and prestripping column separated off on a second side of the dividing wall running essentially in a longitudinal direction of the extraction and prestripping column.

7. The process of claim 2, wherein a gas comprising $C_4$-acetylenes is also desorbed from the bottom fraction.

8. The process of claim 7, wherein the gas comprising $C_4$-acetylenes is taken off as a side offtake stream from the at least one stripping column.

9. The process of claim 7, wherein the gas comprising $C_4$-acetylenes is diluted with uncondensed constituents of vapor from the at least one extraction column.

10. The process of claim 1, wherein the liquid crude $C_4$ fraction comprises
    from 15 to 85% by weight of 1,3-butadiene,
    from 4 to 13% by weight of butanes,
    from 24 to 64% by weight of butanes,
    from 0.2 to 0.5% by weight of $C_4$-acetylenes,
    from 0.01 to 2.0% by weight of $C_3$-hydrocarbons and
    from 0.01 to 0.5% by weight of $C_{5+}$-hydrocarbons.

11. The process of claim 1, wherein the selective solvent comprises at least 80% by weight of N-methylpyrrolidone.

* * * * *